United States Patent [19]

Hervé et al.

[11] Patent Number: 4,581,233

[45] Date of Patent: Apr. 8, 1986

[54] DRUGS BASED ON EXTRACTS OF ALGAE, AND CORRESPONDING FORMULATIONS

[75] Inventors: Rene Hervé, Pludono; Serge Percehais, Saint-Malo, both of France

[73] Assignee: S. A. Goemar, France

[21] Appl. No.: 560,251

[22] Filed: Dec. 9, 1983

Related U.S. Application Data

[63] Continuation of Ser. No. 419,171, Sep. 17, 1982, abandoned.

[30] Foreign Application Priority Data

Sep. 23, 1981 [FR] France ................................ 81 17942

[51] Int. Cl.⁴ ............................................. A61K 35/78
[52] U.S. Cl. .................................................. 424/195.1
[58] Field of Search ............................. 424/195, 195.1

[56] References Cited

U.S. PATENT DOCUMENTS

4,023,734  5/1977  Hervé et al. ......................... 241/17

FOREIGN PATENT DOCUMENTS

693094  7/1967  Belgium .
1485769  6/1967  France .
5526M  1/1968  France .

Primary Examiner—Albert T. Meyers
Assistant Examiner—John W. Rollins
Attorney, Agent, or Firm—Marshall & Melhorn

[57] ABSTRACT

The present invention relates to new drugs based on extracts of algae.

Said extracts consist in "protoexoplasma" obtained by a special method, and which has been found to increase the level of antibodies and to have an antivirus action.

3 Claims, No Drawings

DRUGS BASED ON EXTRACTS OF ALGAE, AND CORRESPONDING FORMULATIONS

This is a continuation of application Ser. No. 419,171, filed Sept. 17, 1982, now abandoned.

The present invention relates to the use in therapeutics of especially prepared extracts of certain algae.

Several families of algae are known to exist.

The algae used according to the present invention belong to the family of the brown algae (or Phaeophyceae) or of the red algae (or Rodophyceae).

The invention more particularly relates to the discovery of unexpected properties in the following algae:

brown algae:
  *Bifurcaria Rotunda*
  *Fucus Vesiculosus*
  *Ascophyllum Nodosum*
  *Pelvetia Canaliculata*
red algae:
  *Delesseria Sanguinea.*

The properties discovered according to the invention are closely related to the special treatment of these algae which leads to a product presenting special physico-chemical characteristics.

The algae are treated as follows:

The algae are collected, and then washed in a pool in order to remove all traces of animalcules and sand.

The algae are thereafter deep-frozen, namely in a plate-type freezer, to $-10°/-30°$ C., in order to preserve the useful elements.

Then they are placed in cold storage for general preservation due to the fact that the crops are seasonal.

The algae are thereafter subjected to a cryogrinding (using for example two grinders in series under liquid nitrogen) and then to a rolling operation (with, for example, a cylinder machine) and finally to a homogenzation. A "mother pulp" is thus obtained of which the constituent particles are approximately between 6 and $20\mu$. Said mother pulp is also called "algae cream".

The said mother pulp can be caused to pass over a decanter at high speed, giving thus two products, on the one hand, the solid part or cake which is called "algae base" and, on the other, the decanted liquor or juice which is called "protoexoplasma of algae".

Alternatively, by way of indication, the said mother pulp can also be used as is.

Also, by way of indication, it is possible to carry out a lyophilization of both the algae cream and protoexoplasma, to obtain a dry form to be subsequently used for producing tablets and the like, for example.

The aforesaid succession of operation is of course applicable to each variety of algae.

To prepare the different extracts, useful reference can be made to French Pat. No. 74/35162 filed on Oct. 18, 1974 in the name of HERVE and ROULLIER.

The cake of algae can be used for example for producing soaps and the like, since it contains about 4 to 6% cellulose, 38 to 40% insoluble alginates, as well as liposoluble vitamins.

But the object of the invention is the use for the aforesaid purposes of the "protoexoplasma" of algae.

The tests which have been conducted have revealed for these products properties increasing in the level of antibodies.

In particular, they revealed an increase in the level of γ-globulins, especially relatively to the immuno-Gs.

The tests were conducted by oral route (in sirup, or drinkable ampoule form).

The products according to the invention have been found to be useful for the treatment of all pathological conditions wherein an increase or preservation of the body resistance is required, and they have been found to cause a long-term immunotherapy. The test conducted on Witstar rats have shown the following properties:

a fair or slight increase of immunoglobuline G (the level of immuno-globulins A and M is not changed and therefore remains normal; this is also the case with the levels of albumin, seromucoid, alpha 1 antitrypsin, haptoglobin, gamma 2 macroglobulin, lipoproteins, transferrin, hemopexin, and beta 1 A globulin).

Without wanting to be in any way restrictive, the Applicant believes that this phenomenon is due to the existence of a correlation between the increase in plasmatic zinc and the increase in immuno-globulins.

no increase of the ACTH (adrenocorticotropic hormone acid), which would seem to introduce an activity where the surrenal glands are concerned.

no increase in the level of FSH (growth hormones).

blood count normal.

reduced albumin/globulin ratio.

metabolism oriented towards anabolism (dosage of amino-metabolites of the methylhistidine type in the urine).

poor secretion of the adrenocorticotropic hormone under the influence of external stimuli (activity foreseeable where the hormonal negative retrocontrol is concerned.

the same phenomenon seems to occur with the somatotropic hormone.

Tests were conducted in rats as indicated hereinabove. A daily dose of 0.02 cc of protoexoplasma of Ascophyllum Nodosum was administered orally per 100 g of body weight.

This protoexoplasma was obtained according to the following method. The brown algae, Ascophyllum Nodosum, were collected, then washed in a pool of sea water to remove all traces of animalcules and sand.

These algae were thereafter deep-frozen in a plate type freezer to $-15°$ C. Then they were placed in cold storage at $-25°$ C. in order to preserve all the useful elements. The algae were subjected to a cyrogrinding by passage through a tower with injection of liquid nitrogen at at $-50°$ C. They were then micro-ground by being sent through 2 cellular grinders cooled from the inside by way of a cooling agent to a temperature below $-20°$ C. The resulting cream was then being homogenized in a tank at room temperature. The mother pulp thus obtained was thereafter caused to pass over a high speed decanter, and the decanted liquor was collected; this liquor being the protoexoplasma; this protoexoplasma has the aspect of a greenish liquid, of density slightly greater than 1. An increase of 10 to 20% of the level of γ-globulins was noted, as well as an increase of 4 to 30% in the weight of the thymus gland (4 to 10% in the females and 10 to 30% in the males) with a doubling of the level of vitamin A in the liver of the treated animals.

A test was also conducted with a patient to whom a dose of 5 to 10 ml of the same protoexoplasma was administered orally every day for one month, morning and evening. At the end of the month, an increase of 40% of the level of γ-globulins was noted.

It was also noted that the albumine/globulin ratio reduces by about 20% during that experiment (1.72→1.38).

ANTIVIRUS ACTIVITY OF *ASCOPHYLLUM NODOSUM* ON HERPES Type I

Titration by the plaque method.

This technique permits to measure with great accuracy, the reduction by a given inhibitor, of the virulence of a virus.

The principle of it is as follows:

Culture jars containing a continuous layer of sensitive cells are inoculated with successive 1/10 dilutions of the virus to be tested. After absorption for one hour, the culture is covered up with agar-agar. The virus multiplies then in the cells where it has penetrated but it cannot be disseminated and infect the remote cells. Therefore there will be no destruction of the cellular layer, and only local lesions (plaques) will be observed, each one being due to an infectious particle.

A series of control boxes is used to determine the titre of the virus which is expressed in plaques-forming units per ml. (P F U/ml).

In the test series, the extract to be tested is added in the culture medium before inoculation of the virus and in the agar-agar.

Experimental conditions:

This test is carried out with an alcoholic extract of Ascophyllum prepared at the laboratory from a grounding of fresh algae; which extract is dry-evaporated, retaken in distilled water and then sterilized by filtering on a Millipore filter.

The filtrate, of which 1 ml corresponds to 1 g of fresh algae is diluted at 1/20, 1/40, 1/200 to measure the reduction of the infectious titre.

RESULTS

|  | VIRUS TITRE P F U/ml | OBSERVATIONS |
| --- | --- | --- |
| CONTROL | 15 × 10$^6$ |  |
| TEST 1/20 | 0 | Limited toxicity |
| TEST 1/40 | 0 | 100% Reduction of titre |
| Test 1/200 | 15 × 10$^6$ | Inactive |

CONCLUSIONS

In a 1/40 dilution, *Ascophyllum Nodosum* has therefore proved to be very efficient since the multiplication of the herpes is completely prevented.

The new drugs according to the invention will therefore be useful in human medicine when administered orally in the dose indicated hereinabove to treat diseases such as herpes and any infections caused by viruses of equivalent nucleic structure.

These new drugs will also be useful in veterinary medicine and will enable for example to reduce the quantity of antibiotics necessary to protect animals, this protection being increased by the increased level of γ-globulins.

What is claimed is:

1. A method for treating humans and domesticated animals to increase the level of γ-globulins at least about 10%, said method comprising:

administering orally protoexoplasma of brown or red algae in an effective amount to increase the γ-globulin level at least about 10%.

2. A method as defined in claim 1 in which the algae is selected from a member of the group consisting of *Bifurcaria Rotunda, Fucus Vesicalosus, Ascophyllum Nodosum, Pelvetin Canaliculata,* and *Delesseria Sanguinea.*

3. A method as claimed in claim 1 wherein the protoexoplasma administered is of *Ascophyllum Nodosum.*

* * * * *